United States Patent [19]

Hamilton et al.

[11] Patent Number: 5,061,603

[45] Date of Patent: Oct. 29, 1991

[54] PHOTOCURABLE COMPOSITIONS

[75] Inventors: John Hamilton, Ramsgate; Peter Dickinson, Broadstairs, both of England

[73] Assignee: Sericol Group Limited, England

[21] Appl. No.: 448,966

[22] Filed: Dec. 12, 1989

[30] Foreign Application Priority Data

Dec. 16, 1988 [GB] United Kingdom ............... 8829359

[51] Int. Cl.[5] ..................... G03F 7/038; G03F 7/028
[52] U.S. Cl. .................................. 430/287; 522/149; 525/59
[58] Field of Search ................... 430/287; 525/59; 522/149

[56] References Cited

U.S. PATENT DOCUMENTS 4,891,300  1/1990  Ichimura et al. ............... 525/59 X
4,920,030  4/1990  Ichimura et al. ............... 522/149 X

FOREIGN PATENT DOCUMENTS 0062446  5/1980  Japan ................................. 430/287

*Primary Examiner*—Cynthia Hamilton
*Attorney, Agent, or Firm*—Bacon & Thomas

[57] ABSTRACT

Photopolymerizable polyvinyl alcohols including a group of formula

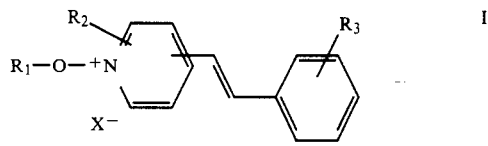

wherein $R_1$ represents a substituted or unsubstituted alkyl group, a substituted or unsubstituted aralkyl group, or a hydrogen atom; $R_2$ represents a substituted or unsubstituted alkyl group, a primary, secondary or tertiary amino group, a cyano, hydroxy or nitro group, a halogen or hydrogen atom or, together with the pyridine ring to which it is attached, part of a quinolyl group; $R_3$ represents a chlorine or hydrogen atom or, together with the benzene ring to which it is attached, part of a naphthyl group; and $X^-$ represents an anion, and photocurable compositions for producing screen printing stencils including such polyvinyl alcohol derivatives. Compositions of the invention show high light sensitivity with low levels of photocrosslinkable groups grafted to the polyvinyl alcohol.

14 Claims, No Drawings

PHOTOCURABLE COMPOSITIONS

This invention concerns photocurable compositions for the production of screen for screen printing.

In screen printing a negative of a print design, known as a stencil, is produced on a mesh of a polymer (usually a polyester) or of stainless steel stretched over a wooden or metal frame, the areas of mesh where printing is not to be effected (stencil areas) being covered with a material impervious to the ink to be used for the printing.

Many methods have been proposed for the production of screen printing stencils. Stencils can be prepared either independently of the screen, by the indirect film method, or on the screen itself by the direct method.

In the indirect method, a photosensitive layer is coated on to a temporary support sheet, usually a transparent polyester sheet, and following exposure to actinic light the layer is developed on the support sheet using water to remove unexposed areas of the photosensitive layer. The wet stencil on its support is then adhered to the screen mesh by the application of gentle, even pressure, and, after drying, the support sheet is removed, leaving the stencil on the screen mesh ready for printing.

In the direct method, a photosensitive emulsion is coated on to a mesh and dried to give a continuous, even film. A stencil is then produced by imaging the coating photographically through a line or half tone positive and then developing an image with a spray of water, again to remove unexposed areas of the film.

A further technique, the so-called capillary film ethod, involves the application of a photosensitive layer to a polyester sheet which is then transferred to a mesh prior to imaging. Imaging and development are then effected as described for the direct method.

Combinations of emulsions and films are also possible in which a direct emulsion is used to adhere a film to a mesh. Development of the stencil is then as with the direct method.

The photosensitive coatings for all of these techniques are polymer-based, and their formulation is important to achieve chemical and thermal resistance in use and during manufacture, dimensional stability, flexibility, maintenance of light Compositions used to prepare screen printing stencils are in general based on water soluble colloids acting as binder resins, usually polyvinyl alcohol in the case of direct emulsions and capillary films. The compositions are such that those areas of the coatings irradiated by actinic light remain on the screen after development, as they become insoluble in water, while those areas protected from actinic light retain their water solubility and are easily washed away on development.

Image development necessitates rendering insoluble to water a coating of a water soluble colloid, either by crosslinking the colloid or by forming a secondary polymer matrix within the coating structure, thereby preventing redispersion of the colloid during subsequent aqueous development.

Crosslinking of colloids can be achieved by a number of methods using ultra violet radiation. Colloidal polymer molecules having reactive groups along the polymer chain can crosslink with other polymer molecules via such groups. Alternatively, some reactive groups require an intermediate crosslinking agent. The accompanying increase in molecular weight of the colloid, due to photopolymerisation, changes the physical character of the polymer so as radically to reduce its solubility in water.

Secondary polymer matrices are formed by dispersing photopolymerisable monomers and/or oligomers in the aqueous colloidal solution, coating it to form a film, and exposing it to ultra violet radiation.

A secondary polymer matrix insoluble in water is formed by photopolymerising compositions containing photopolymerisable monomers and/or oligomers possessing light sensitive groups. Oligomers are preferred because the rate of insolubilisation of the compositions on exposure is usually more rapid, presumably due to a rapid establishment of a network polymer structure and also because of their lower rate of evaporation on drying. Their outstanding performance as low molecular weight addition polymerisable components is due to a plurality of addition polymerisable linkages, terminal linkages being particularly reactive.

Important requirements for colloidal binder resins for producing screen printing stencils are solvent resistance, decoatability and water solubility. Polyvinyl alcohol derivatives meet all of these requirements as well as having good mechanical strength and heat resistance. The decoating of polyvinyl alcohol derivatives can simply be achieved by selectively oxidising 1,2-diol groups on the polymer chain using a periodate. Small amounts (up to 2%) of hydroxy groups on polyvinyl alcohol chains are present as 1,2-diol groups. It has been suggested that their occurrence depends on the temperature at which the polymerisation of the vinyl acetate used to form the polyvinyl alcohol is effected, polyvinyl alcohol being obtained from polyvinyl acetate by saponification.

The water solubility of polyvinyl alcohol derivatives is related both to their molecular weight and to their degree of hydrolysis. In general, they are rendered water soluble when at least 70% of the acetate groups of the precursor polyvinyl acetate are hydrolysed to hydroxy groups. Larger numbers of acetate groups result in the polymer having hydrophobic portions which repel the infusion of water. Conversely, totally hydrolysed polyvinyl alcohols are only slightly soluble in cold water as a result of strong intermolecular hydrogen bonding which imparts a high level of crystallinity to the solid resins. Lower molecular weight grades of polyvinyl alcohol tend to have a greater solubility in water than do higher molecular weight grades.

Photocrosslinkable compositions using polyvinyl alcohol suitable for producing screen printing stencils are well known in the art. Original systems were photosensitised immediately priot to use by adding a dichromate compound or a polymeric diazonium salt. These compositions have the disadvantage of beign supplied as two packs, one consisting of a sensitiser and the other a base colloid. After mixing, the compositions usually have a useful pot-life of a matter of days when the sensitiser is a dichromate, and a maximum of three months when the sensitiser is a polymeric diazonium salt. When sensitised emulsion is stored for longer periods under conditions of normal temperature and humidity, a so-called dark reaction occurs which makes even unexposed areas of the film insoluble in water. Furthermore, compositions containing chromium compounds are undesirable because they are irritant and present environmental problems due to their toxicity.

Another disadvantage of dichromate and diazonium salt sensitised compositions is the limited life of unexposed screens produced from them. The sensitivity of the compositions also varies with temperature, age and relative humidity. Many attempts have been made to overcome these various disadvantages, for example by the replacement of dichromate or diazonium salt photosentisers by more stable sensitisers.

Improved photosensitive compositions can be produced by reacting the polyvinyl alcohol with a compound having a photocrosslinkable group or by dispersing a photocrosslinkable unsaturated or epoxy monomer or oligomer in the polyvinyl alcohol. A combination of both approaches has also been suggested.

U.S. Pat. No. 2,610,120 describes light sensitive photocrosslinkable polyvinyl alcohol derivatives obtained by esterifying the hydroxy groups of the polyvinyl alcohol with a cinnamoyl halide. However, the high levels of cinnamoyl groups needed for crosslinking decrease the number of hydroxy groups to such an extent that the compositions derived from them show a remarkable decrease in water developability and are therefore unsuitable for aqueous systems. These systems also have the disadvantage of requiring spectral sensitisation to increase their sensitivity to the actinic light emitted from metal halide lamps normally used in screen printing stencil production even though they will crosslink under the influence of ultraviolet light.

British Patent Specification 2030575 describes photopolymerisable compositions containing polyvinyl alcohol having grafted N-methylstyrylpyridinium groups. These groups overcome disadvantages of grafted cinnamate groups since they maintain the solubility of the polyvinyl alcohol when grafted at low levels. N-methylstyrylpyridinium groups are self-sensitising, but the level of N-methylstyrylpyridinium groups which can be grafted while maintaining water solubility is very limited. However, a high degree of photosensitivity can be achieved at extremely low concentrations of such groups. The photopolymer therefore retains many of the properties of the original polyvinyl alcohol. One consequence of this is that crosslinked stencils can easily be decoated with a periodate. Compositions of this type have exhibited poor adhesion to the mesh, and the choice of anion is limited to those of strong acids.

European Patent Specification 92901 describes polyvinyl alcohol having pendant chalcone groups as photocrosslinkable groups. These photopolymers can be prepared in high yield from readily available and inexpensive starting materials, and their structures can easily be varied in order to select a U.V. absorption wavelength at or about a desired value to match the spectral emission characteristics of the light source used for exposure. However, these systems have the disadvantage that the rate of photocrosslinking is slow, requiring long exposure times when printing screens are being made.

European Patent Specification 130804 describes compositions including polyvinyl alcohol having grafted N-methylstyrylpyridinium groups, a free-radical photopolymerisable, ethylenically-unsaturated compound, and a free-radical photopolymerisation initiator. Water-dispersible polymers or hydrophobic polymers can also be added. These compositions produce stencils which have good solvent resistance, water resistance and abrasion resistance. The use of polyvinyl alcohol with grafted N-methylstyrylpyridinium groups serves to facilitate dispersion of the photopolymerisable unsaturated compound. Again, the choice of anions is limited to those of strong acids. The anionic water soluble thioxanthenone derivatives described in British Patent Specification 2lOS979 cannot be used in such compositions as free radical photopolymerisation initiators since gel formation occurs.

European Patent Specification 252150 highlights another disadvantage of compositions of the type described in British Patent Specification 2030185 and European Patent Specification 92901. In particular, the adhesion of cured compositions containing grafted polyvinyl alcohol of the types described in these Specifications have insufficient adhesion to form stencils and this can cause peeling of the cured stencil during development by spraying with water. Another disadvantage of these compositions is the absence of a color change to give a visible image after exposure of coatings of the compositions. Diazonium salts can be used to overcome these problems but this is unsuitable for the production of high quality stencils. Short pot lives can also result from the use of certain diazo compounds.

According to the present invention there are provided grafted photopolymerisable polyvinyl alcohols including a group of formula

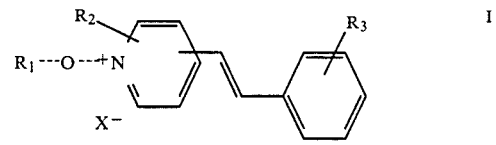

wherein $R_1$ represents a substituted or unsubstituted alkyl group, a substituted or unsubstituted aralkyl group, or a hydrogen atom; $R_2$ represents a substituted or unsubstituted alkyl group, a primary, secondary or tertiary amino group, a cyano group, a hydroxy group, a nitro group, a halogen or hydrogen atom or, together with the pyridine ring to which it is attached, part of a quinolyl group; $R_3$ represents a chlorine or hydrogen atom or, together with the benzene ring to which it is attached, part of a naphthyl group; and X represents an anion.

The present invention also provides compositions for producing screen printing stencils, the compositions comprising a grafted polyvinyl alcohol in accordance with the invention.

Compositions of this invention have exhibited high sensitivity to light whilst having low levels of photocrosslinkable groups grafted to the polyvinyl alcohol. The high water solubility exhibited by grafted photopolymerisable polyvinyl alcohols of the invention, especially those including grafted N-methoxy-4-styrylpyridinium groups, has enabled a wider range of soluble polyvinyl alcohol derivatives to be produced than has hitherto been possible by grafting N-methyl-4-styrylpyridinium groups.

Particularly preferred compositions of the present invention include a fluorescein derivative, for example eosin Y (2,4,5,7-tetrabromofluorescein disodium salt) or the tetra-iodo analogue, erythrosin B. Such compositions have surprisingly revealed a visible latent image which can be observed on a printing screen after exposure of the compositions to actinic light but before development with water, this resulting from a color change in exposed areas of the compositions. Preferred amounts of fluorescein derivative are from 0.05 to 0.5, advantageously about 0.1% based on the weight of the compositions. Analogous compositions containing polyvinyl alcohol with grafted N-methyl-4-styrylpyridinium groups have not exhibited such a color change. When substituted, $R_1$ can represent an alkoxyalkyl group. However, $R_1$ preferably represents a substituted or unsubstituted lower $C_{1-3}$ alkyl group. Especially preferred groups of formula I are those in which $R_1$ represents a ethyl or propyl group. $R_2$ and $R_3$ each preferably represent a hydrogen atom. In particularly preferred grafted alcohol derivatives of the present invention formula I represents an N-methoxy-4-styrylpyridinium group. It is also preferred that the groups of formula I be grafted to the polyvinyl alcohol through the 4-position of the benzene ring of formula I.

Grafted polyvinyl alcohol derivatives of the present invention wherein $R_1$ represents a methyl group are preferred as less gelling has been observed than with prior art grafted polyvinyl alcohol derivatives of British Patent Specification 2030575. This allows higher levels of grafting, for example for improving the water resistance of stencils produced therefrom.

The anion X can be selected from a wide range of anions, in particular to modify solubility of the salts, for example it can represent chloride, bromide, iodide, perchlorate, tetrafluoroborate, phosphate, methylsulfate, phosphate, sulfate, methanesulfonate, or benzene or substituted benzene sulfonate ions. A wide range of surfactant anions can surprisingly be used, for example alkylbenzene sulfonate, alcohol sulfate, ether sulfate, phosphate ester, sulfosuccinate, sulfosuccinamate, alkane sulfonate, sarcosinate, taurate or isethionate ions. Surfactant anions have been particularly effective in providing compositions of the invention with good light sensitivity. Surfactant anions can also be selected to improve adhesion of compositions of the invention to screen meshes.

The groups of formula I can be linked to the polyvinyl alcohol by a variety of linking groups. Examples of linking groups which can be used include acetal and ester groups, acetal groups being preferred. The linking groups can also include one or more alkylene oxide groups.

Known methods can be used to produce grafted polyvinyl alcohols of the present invention, the method used depending on the type of linking grou which is formed.

Acetal linkages can be produced from the corresponding aldehyde including a group of formula I, for example analogously to the method described in British Patent Specification 2030575. Ester linkages can be prepared from the corresponding acid including a group of formula I, or a functional derivative thereof, for example analogously to the method described in U.S. Pat. No. 2,610,120. Alkylene oxide groups can, for example, be formed by reaction of a haloacetaldehyde or a haloacetic acid with the appropriate phenol containing the desired group of formula I. Acetal or ester formation can then be effected in known manner from the resulting reaction product.

The polyvinyl alcohol can be partially or fully hydrolysed polyvinyl acetate, and it can contain acetyl groups. The average degree of polymerisation is preferably from 350 to 2500. The degree of hydrolysis of the polyvinyl alcohol is preferably from 72 to 99%, i.e. derived from polyvinyl acetate. A mixture of polyvinyl alcohol derivatives can be used having different degrees of polymerisation and/or hydrolysis. The polyvinyl alcohol can, for example, be of a type proposed hitherto for use in screen printing. Other water-soluble polymers containing units derived from vinyl alcohol can be used, e.g. copolymers with unsaturated carboxylic acids and their salt.

Compositions of the present invention preferably contain up to 30% by weight of a grafted polyvinyl alcohol of the present invention.

A further advantage of compositions of the invention having groups of formula I in which $R_1$ represents a methyl group is that they can fragment analogously to the mechanism described in U.S. Pat. No. 3,745,009. This fragmentation can generate free radicals which can in turn initiate polymerisation of an ethylenically unsaturated secondary polymer matrix when such is present.

Other materials which can be included in compositions of the present invention include fillers and/or extenders, for example for increasing the solids content of the compositions and additives which improve the performance of the compositions. Fillers and/or extenders can be used to increase the thickness or build of layers of compositions of the invention when they are used to form a screen printing stencils. Various fillers and/or extenders can be used, and they can be inert, film-formable or photopolymerisable in their own right. Suitable inert fillers for increasing the solids content of the compositions include starch, kaolin, polytetrafluoroethylene, titanium dioxide, silica and talc.

Hydrophobic polymers can also be added to compositions of the present invention, for example in the form of an aqueous dispersion solubilised by a surfactant or a water soluble colloid. Polyvinyl alcohol is particularly preferred as the water soluble colloid. These dispersions in general have the property of forming a cohesive film when dry, thereby binding fillers and pigments and promoting their adhesion to the screen mesh or other substrate. In addition, polymer dispersions can be produced with high solids contents, e.g. up to 70% by weight, without imparting an excessively high viscosity to compositions of the invention. This can enable improved compositions to be prepared. Examples of polymer dispersions which can be included in compositions of the present invention include those of polyvinyl acetate, vinyl acetate/ethylene copolymers, vinyl acetate/acrylic ester copolymers, and styrene/butadiene copolymers.

Other ohotopolymerisable materials can be added to compositions of the present invention These materials can be used to produce a secondary matrix within a layer of the compositions, this secondary matrix generally serving to enhance the properties of the layer. Materials having this property have been proposed hitherto, but they should be selected and formulated carefully so that the advantages of grafting of the polyvinyl alcohol are not lost. Hydrophobic or hydrophilic unsaturated compounds can be dissolved or dispersed in the compositions of the present invention Hydrophobic and sparingly soluble compounds will usually be dissolved in a solvent compatible with the grafted polyvinyl alcohol. Compounds having at least two photocrosslinkable groups are especially preferred because crosslinked products with good solvent resistance have been obtained, for example pentaerythritol triacrylate, pentaerythritol trimethacrylate, pentaerythritol tetracrylate, trimethylolpropane triacrylate, tripropyleneglycol diacrylate and triethyleneglycol diacrylate.

Hydrophilic unsaturated compounds which can be used include those having an affinity for polyvinyl alcohol, and they can also serve to provide a continuous polyvinyl alcohol phase in the compositions of the invention. Examples of such materials include N-vinylpyrrolidone, polyethylene glycol 200 diacrylate, and Lankro RCP 2685, 2701, 2785 and 2850 (water thinnable UV curable acrylate resins).

Polyfunctional acrylate and methacrylate oligomers described in U.S Pat. No. 4,621,044 can also be used in compositions of the present invention, the grafted polyvinyl alcohol in general being compatible with such oligomers over a much wider range of concentrations than the polymers described in U.S. Pat. No. 4,621,044. Furthermore, these oligomers have imparted improved flexibility to cured compositions of the present invention Where compositions according to the present invention contain other photopolymerisable materials, a photoinitiator is usually required.

The photoinitiator can be selected from photoinitiators proposed for the free radical polymerisation of unsaturated compounds by exposure to actinic light. However, since the compositions of the present invention will usually be exposed to actinic light through glass, it is preferred that the photoinitiator absorbs at a wavelength above 325nm. Preferred photoinitiators include thioxanthenone derivatives, substituted benzophenones and benzils, and acyl phosphine oxides. Particularly preferred photoinitiators are thioxanthenones, e.g. 2-hydroxy-3-(3,4-dimethyl-9-oxo-9H-thioxanthenone-2-yloxy)-N,N,N-trimethyl-1-propanaminium chloride, trimethyl-1-propanaminium chloride and anionic derivatives of the type described in British Patent Specification 2108979-A, e.g. the sodium salt of 2-(3-sulfopropoxy)-thioxanthenone. Other photoinitiators which can be used include benzophenone derivatives, e.g. 4-benzoyl-benzyl trimethylammonium chloride, or benzil derivatives, e.g. sodium 4-(sulfomethyl)-benzil The photosensitivity of such compositions of the present invention can be further increased by the inclusion of an accelerator, preferably a tertiary amine when a thioxanthenone or benzophenone photoinitiator is used. Preferred tertiary amines contain at least one group derived from an aliphatic alcohol, for example N-methyl-diethanolamine or N,N-dimethylethanolamine. The preferred amount of accelerator is from 0.1% to 8%, more preferably from 1 to 5%, by weight of the composition.

Compositions of the invention can also contain emulsion stabilisers, wetting agents, defoaming agents or plasticisers to improve their overall performance. In addition, it is usually preferred to include an inhibitor of thermal polymerisation. Furthermore, dyes or pigments can be included to provide visible screens from the compositions.

The photosensitive compositions of the present invention can be used as photoresists for many applications.

The following Preparations and Examples are given by way of illustration only. All parts are by weight unless stated otherwise.

PREPARATION 1

50 parts of a 30% by weight aqueous hydrogen peroxide solution were added to a solution of 47 parts of 4-methylpyridine in 300 parts of glacial acetic acid, and the mixture was heated on a water bath at 70° to 80° C. After three hours, a further 35 parts of hydrogen peroxide solution were added and the mixture was maintained at the same temperature for an additional nine hours. The mixture was then evaporated under vacuum, diluted with 100 parts of water, and finally evaporated to give a very viscous liquid residue. This residue was made strongly alkaline with anhydrous sodium carbonate, shaken with 300 parts by weight of chloroform, and the mixture was filtered. The filtrate was dried over anhydrous sodium sulfate and vacuum evaporated. The resulting solid 4-methylpyridine-N-oxide was recrystallised from ethanol.

PREPARATION 2

A mixture of 11 parts of 4-methylpyridine-N-oxide and 28 parts of methyl 4-methylbenzene sulfonate was heated on a steam bath, with constant stirring, until an exothermic reaction started. The heating was stopped, and the temperature of the mixture increased to a maximum of about 120° C. The mixture was allowed to cool, and it was diluted with 150 parts of acetone and refrigerated. The solid N-methoxy-4-methylpyridinium 4-methylbenzene sulfonate which separated was collected by filtration and washed with acetone.

PREPARATION 3

15 parts of N-methoxy-4-methylpyridinium 4-methylbenzene sulfonate and 7 parts of terephthaldehyde were dissolved in a mixture of 7.8 parts of propan-2-ol and 9.4 parts of 2-methoxyethyl ether. 1 part of a 90% by weight aqueous solution of triethanolamine was added, and the mixture was placed in an ultrasonic bath for 12 hours. After being left to stand at room temperature for 12 hours, a solid product precipitated. The N-methoxy-4-(4-formylstyryl)pyridinium 4-methylbenzene sulfonate was filtered off, washed with acetone and vacuum dried.

Second Method 29 parts of N-methoxy-4-methylpyridinium 4-methylbenzene sulfonate and 13.4 parts of terephthaldehyde were dissolved in a mixture of 31.2 parts of propan-2-ol and 18.6 parts of 2-methoxyethyl ether. 5.1 parts of piperidine were added to the solution, and the mixture was heated on a steam bath for twelve hours. After cooling the mixture, it was partitioned between dichloromethane and water. The aqueous layer was evaporated and refrigerated overnight. It was then allowed to return to room temperature, diluted with acetone, and the precipitated solid N-methoxy-4-(formylstyryl)-pyridinium 4-methylbenzene sulfonate was filtered off and air dried.

EXAMPLE 1

Two substantially identical grafted polyvinyl alcohols were compared, one being in accordance with the invention and having grafted N-methoxy-4-(4-formylstyryl)pyridinium groups and the other having grafted N-methyl-4-(4-formylstyryl)pyridinium groups. The grafted polyvinyl alcohols were prepared by mixing 100 parts by weight of a 13% by weight aqueous solution of polyvinyl alcohol (Gohsenol GH23 - ex Nippon Gosei) with 1 part of the appropriate N-substituted-4-(4-formylstyryl)pyridinium methylsulfate dissolved in 2 parts of water. The viscosities of the resulting mixtures were adjusted to 83 poise by the addition of small amounts of water. Each mixture was then acidified with 0.3 parts of naphthalene-1-sulfonic acid.

The viscosities of the two mixtures were then compared after storage of the mixtures under identical conditions.

TABLE 1

| | Viscosity of mixture containing | |
| --- | --- | --- |
| | N-methyl compound | N-methoxy compound |
| Initially | 83 | 83 |
| 3.5 hrs. - 70° C. | 135 | 27.5 |
| 3.5 hrs. - 25° C. | gel | 152 |

The mixture containing the polyvinyl alcohol in accordance with the invention having grafted N-methoxypyridylstyryl groups had a lower viscosity under the above storage conditions than the corresponding mixture containing a prior art polyvinyl alcohol with grafted N-methylpyridylstyryl groups. Compositions in accordance with the invention can therefore be used under a wider variety of conditions than can hitherto proposed compositions.

EXAMPLE 2

15 parts of a 13% by weight aqueous solution of polyvinyl alcohol (Gohsenol GH20 - ex Nippon Gosei) were mixed with 0.2 part of N-methoxy-4-(4-formylstyryl)pyridinium 4-methylbenzene sulfonate dissolved in 1 part of water. The mixture was adjusted to pH 2 by the addition of about 0.2 part of naphthalene-1-sulfonic acid, and the mixture was heated at 70° C for 17 hours.

The resulting product was evaluated as a screen stencil composition by applying it to a 120 threads per cm screen mesh using two coats wet on wet on each side of the mesh. The coating was dried and exposed for 200 seconds through a photographic positive transparency to a 3 kW metal halide doped mercury halide lamp (Theimer) at a distance of 1.2m. After washing the mesh with water to remove uncured coating material, a relief stencil image was obtained which was very water resistant.

The composition was further evaluated in a simple stencil making formulation. 10 parts of the grafted polyvinyl alcohol solution were mixed with 4 parts of a 55% by weight aqueous dispersion of polyvinyl acetate and colored with a pigment dispersion (Unisperse Blue GE (90%)). The resulting composition was subjected to the procedure described above, with exposure for 100 seconds, to produce a relief stencil image showing good resistance to water and good build thickness) above and below the mesh.

EXAMPLE 3

Batches of solutions of grafted polyvinyl alcohol were prepared as follows using various surfactant anions.

80 parts of a 13% by weight aqueous solution of polyvinyl alcohol (Gohsenol GH20) were mixed with 1g of N-methoxy-4-(4-formylstyryl)pyridinium 4-methylbenzene sulfonate dissolved in 2 parts of water. The mixture was adjusted to pH 2 by the addition of 90% phosphoric acid solution and the mixture was heated at 70° C. for 5 hours. 10g of ion exchange resin (Amberlyst 21 - ex BDH) were added to the mixture, and the mixture was left to stand overnight. The ion exchange resin was then filtered off to give a solution of a photosensitive grafted polyvinyl alcohol. Solutions of anionic surfactants were then added to portions of the grafted polyvinyl alcohol solution, and the mixtures were evaluated as follows:

15 parts of a grafted polyvinyl alcohol solution, 0.5 part of a surfactant solution (where the surfactant was solid, 0.5 part of the solid was dissolved in 1 to 2 parts of water) and 5 parts of a 55% by weight aqueous solution of polyvinyl acetate were mixed using a low speed stirrer and then colored with a pigment dispersion (Unisperse Blue GE (90%)).

The resulting compositions were subjected to the procedure of Example 1 using one coat on each side of the mesh. After exposure, the ease of washout of the uncured coating and the water resistance of the cured parts of the coating (stencil areas) were assessed. The results are summarised in the following Table.

TABLE 2

| Surfactant Anion | Trade Name | Supplier | Ease of Washout | Water Resistance of Stencil |
| --- | --- | --- | --- | --- |
| Alcohol sulfate | Empicol LX28 | Albright & Wilson | Very easy | Satisfactory |
| Ether sulfate | Solumin FP 85 50 | A.B.M. Chemicals | Very easy | Satisfactory |
| Phosphate ester | Monofax 786 | D.F. Anstead | Very easy | Satisfactory |
| Alkane sulfonate | Hostapur SAS60 | Hoechst UK | Very easy | Satisfactory |
| Laurate | — | A.B.M. Chemicals | Very easy | Very resistant |
| Polyacrylate | Glopol LS6 | A.B.M. Chemicals | Very easy | Satisfactory |
| Sarcosinate | Crodasinic L | Croda Chemicals | Very easy | Satisfactory |
| 4-Styrene sulfonate | — | Aldrich Chemical Co | Very easy | Very resistant |

EXAMPLE 4

25 parts of grafted polyvinyl alcohol solution from Example 3 were mixed with 1.2 parts of a sulfosuccinate surfactant (Pentron S127 - ex ABM Chemicals) and 17.5 parts of a 55% by weight aqueous dispersion of polyvinyl acetate. 2.5 parts of an 80% by weight solution of the diacrylate of bisphenol-A-diglycidyl ether in tripropylene glycol diacrylate, 0.1 part of 2-isopropylthioxanthone and 0.05 part of ethyl 4-dimethylaminobenzoate were mixed until a homogeneous mixture had been obtained. This mixture was then added with stirring to the mixture prepared above. The composition obtained was colored with a pigment dispersion (Unisperse Blue GE (90%)).

The resulting composition was subjected to the procedure of Example 1 with exposure for up to 100 seconds through an Autotype calculator. Relief images were obtained for exposures equivalent to 25, 33, 50 and 75 seconds. Exposures of 50 seconds and greater gave satisfactory stencils.

EXAMPLE 5

10 parts of a solution of polyvinyl alcohol having N-methoxy-4-(4-formyl-styryl)pyridinium groups grafted via acetal groups and prepared as in Example 3 were mixed with 0.05 part of eosin Y (Aldrich Chemical co.). The mixture was coated on to a 120 threads per cm. screen mesh using two coats wet on wet on each side of the mesh, and the coatings were allowed to dry.

An identical mixture was prepared from 10 parts of a solution of polyvinyl alcohol having N-methyl groups in place of the N-methoxy groups, and 0.05 part of eosin Y, and the mixture was used to coat a screen mesh as described above.

Both coatings were exposed for 70 seconds through photographic positives using a Nuarc FT26V3UP exposure unit.

After exposure, before washout to effect development of the image, the screens were observed under visible light. The screen produced from the composition containing N-methoxy groups in the grafted groups of formula I could be seen whereas no visible image could be seen with the comparison screen having N-methyl groups in the grafted groups.

EXAMPLE 6

100 g samples of 13% by weight aqueous solutions of polyvinyl alcohol having respectively N-methoxypyridinium and N-methylpyridinium groups grafted thereto were mixed with 0.4g of the sodium salt of 2-(3-sulfopropoxy)thioxanthenone. The stabilities of these mixtures were measured initially, and after three days, and the results were as follows:

|  | N-methoxystyryl derivative | N-methoxystyryl derivative |
| --- | --- | --- |
| Initial viscosity (Poise) | 104 | 104 |
| 3 days after mixing (Poise) | 113 | 170 |

The viscosity of the N-methoxystyryl grafted polyvinyl alcohol of the invention increased to a very considerably lesser extent than the prior art N-methylstyryl grafted polyvinyl alcohol after storage of the respective mixtures for three days. This was due to lack of gel formation in the polyvinyl alcohol derivative of the invention, whereas gel formation did occur with the prior art grafted polyvinyl alcohol.

We claim:

1. Photopolymerisable grafted polyvinyl alcohol including grafted thereto groups of formula

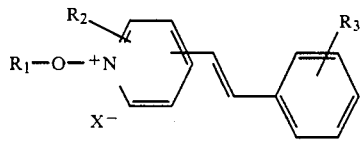

I wherein $R_1$ represents a substituted or unsubstituted alkyl group or a substituted or unsubstituted aralkyl group; $R_2$ represents a substituted or unsubstituted alkyl group, a primary, secondary or tertiary amino group, a cyano group, a hydroxy group, a nitro group, a halogen or hydrogen atom or, together with the pyridine ring to which it is attached, part of a quinolyl group; $R_3$ represents a chlorine or hydrogen atom or, together with the benzene ring to which it is attached, part of a naphthyl gruop; and $X^-$ represents an anion.

2. Photopolymerisable grafted polyvinyl alcohol according to claim 1, wherein $R_1$ represents a methyl group.

3. Photopolymerisable grafted polyvinyl alcohol according to claim 1, wherein $R_2$ represents a hydrogen atom.

4. Photopolymerisable grafted polyvinyl alcohol according to claim 1, wherein $R_3$ represents a hydrogen atom.

5. Photopolymerisable grafted polyvinyl alcohol according to claim 1, wherein the group of formula I is a N-methoxy-4-styrylpyridinium group.

6. Photopolymerisable grafted polyvinyl alcohol according to claim 1, wherein the group of formula I is grafted to the polyvinyl alcohol by an acetal group.

7. Photopolymerisable grafted polyvinyl alcohol according to claim 1, wherein the group of formula I is grafted to the polyvinyl alcohol through the 4-position of the benzene ring of the styryl group.

8. Photopolymerisable grafted polyvinyl alcohol according to claim 1, wherein up to 20% of the hydroxy groups of the polyvinyl alcohol have groups of formula I grafted thereto.

9. Photopolymerisable grafted polyvinyl alcohol according to claim 1, wherein the polyvinyl alcohol is hydrolysed polyvinyl acetate with a degree of hydrolysis of from 72 to 99%.

10. Compositions for producing screens for screen printing, the compositions comprising a photocurable grafted polyvinyl alcohol according to claim 1.

11. Compositions according to claim 10, containing up to 30% by weight of the grafted polyvinyl alcohol.

12. Compositions according to claim 10, containing a filler.

13. Compositions according to claim 10, containing a photopolymerisable, ethylenically-unsaturated compound.

14. Compositions according to claim 10, containing eosin Y.

* * * * *